US 8,565,900 B2

(12) United States Patent
Hochmair et al.

(10) Patent No.: US 8,565,900 B2
(45) Date of Patent: *Oct. 22, 2013

(54) LOW POWER SIGNAL TRANSMISSION

(71) Applicant: MED-EL Elektromedizinische Geraete GmbH, Innsbruck (AT)

(72) Inventors: Erwin Hochmair, Axams (AT); Ingeborg Hochmair, Axams (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 0 days.

This patent is subject to a terminal disclaimer.

(21) Appl. No.: 13/751,676

(22) Filed: Jan. 28, 2013

(65) Prior Publication Data

US 2013/0138195 A1    May 30, 2013

Related U.S. Application Data

(60) Continuation of application No. 12/652,335, filed on Jan. 5, 2010, now Pat. No. 8,363,867, which is a division of application No. 10/452,828, filed on Jun. 2, 2003, now Pat. No. 7,657,045.

(60) Provisional application No. 60/384,948, filed on May 31, 2002.

(51) Int. Cl.
*A61N 1/00* (2006.01)

(52) U.S. Cl.
USPC .......................................................... 607/137

(58) Field of Classification Search
USPC ................... 607/137; 330/276; 600/25
See application file for complete search history.

(56) References Cited

U.S. PATENT DOCUMENTS

| 4,519,396 A | 5/1985 | Epstein et al. ............... 128/698 |
| 4,624,143 A | 11/1986 | Green ............................ 73/620 |
| 5,721,783 A | 2/1998 | Anderson ...................... 381/68 |
| 5,824,022 A | 10/1998 | Zilberman et al. ............ 607/57 |
| 5,991,419 A | 11/1999 | Brander ........................ 381/312 |

(Continued)

FOREIGN PATENT DOCUMENTS

| EP | 1124211 | 8/2001 |
| EP | 2520330 | 11/2012 |

(Continued)

OTHER PUBLICATIONS

McDermott, "A Programmable Sound Processor for Advanced Hearing Aid Research", IEEE Transactions on Rehabilitation Engineering, vol. 6, No. 1, Mar. 1998, pp. 53-59.

(Continued)

*Primary Examiner* — Robert N Wieland
(74) *Attorney, Agent, or Firm* — Sunstein Kann Murphy & Timbers LLP

(57) ABSTRACT

A low-power implant system. The system includes an implant for implantation into a person, such as a cochlear implant or a middle ear implant. The implant is capable of communicating with a device via transmission of ultra wideband pulses. The device may be adapted to be worn external to the person, or may be a second implant. So as to conserve battery power, the transmitted ultra wideband pulses may have a low duty cycle of approximately 1/1000 or less. Power savings may also be realized by using time-gating amplifiers in the implant and/or device receiver.

20 Claims, 10 Drawing Sheets

(56) References Cited

U.S. PATENT DOCUMENTS

| | | | |
|---|---|---|---|
| 5,997,466 A * | 12/1999 | Adams et al. | 600/25 |
| 5,999,830 A | 12/1999 | Taniguchi et al. | 455/574 |
| 6,021,207 A | 2/2000 | Puthuff et al. | 381/330 |
| 6,026,125 A | 2/2000 | Larrick et al. | 375/295 |
| 6,031,862 A | 2/2000 | Fullerton et al. | 375/200 |
| 6,261,224 B1 | 7/2001 | Adams et al. | 600/25 |
| 6,351,652 B1 | 2/2002 | Finn et al. | 455/552 |
| 6,388,609 B2 | 5/2002 | Paese et al. | 342/27 |
| 6,512,455 B2 | 1/2003 | Finn et al. | 340/572.1 |
| 6,556,621 B1 | 4/2003 | Richards et al. | 375/150 |
| 7,206,640 B1 | 4/2007 | Overstreet | 607/57 |
| 7,209,523 B1 | 4/2007 | Larrick et al. | 375/295 |
| 7,657,045 B2 | 2/2010 | Hochmair et al. | 381/312 |
| 8,363,867 B2 | 1/2013 | Hochmair et al. | 381/312 |
| 2001/0047314 A1 | 11/2001 | Linberg | 705/28 |
| 2001/0051766 A1 | 12/2001 | Gazdzinski | 600/309 |
| 2003/0011433 A1* | 1/2003 | Richley | 330/276 |
| 2004/0202339 A1 | 10/2004 | O'Brien et al. | 381/312 |
| 2007/0121975 A1 | 5/2007 | Sacha et al. | 381/312 |

FOREIGN PATENT DOCUMENTS

| | | |
|---|---|---|
| WO | WO 96/09694 | 3/1996 |
| WO | WO 99/06108 | 2/1999 |
| WO | WO 00/54237 | 9/2000 |
| WO | WO 01/24393 | 4/2001 |
| WO | WO 01/43818 | 6/2001 |
| WO | WO 02/09363 | 1/2002 |
| WO | WO 03/101536 | 12/2003 |

OTHER PUBLICATIONS

International Searching Authority, International Search Report—International Application No. PCT/IB03/02783, dated Sep. 11, 2003, 3 pages.

European Patent Office, European Search Report—European Application No. 12178943.2-1265, dated Sep. 20, 2012, together with the European Search Opinion of the European Patent Office, 7 pages.

* cited by examiner

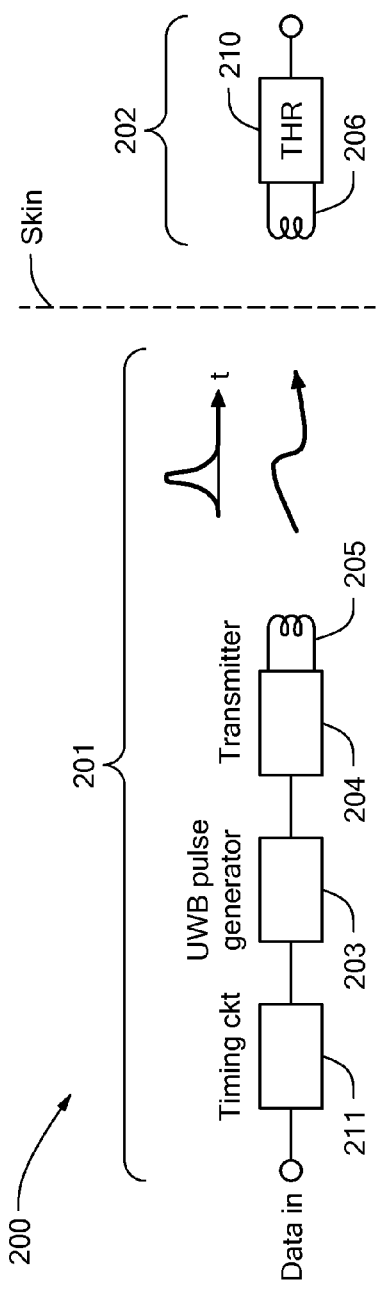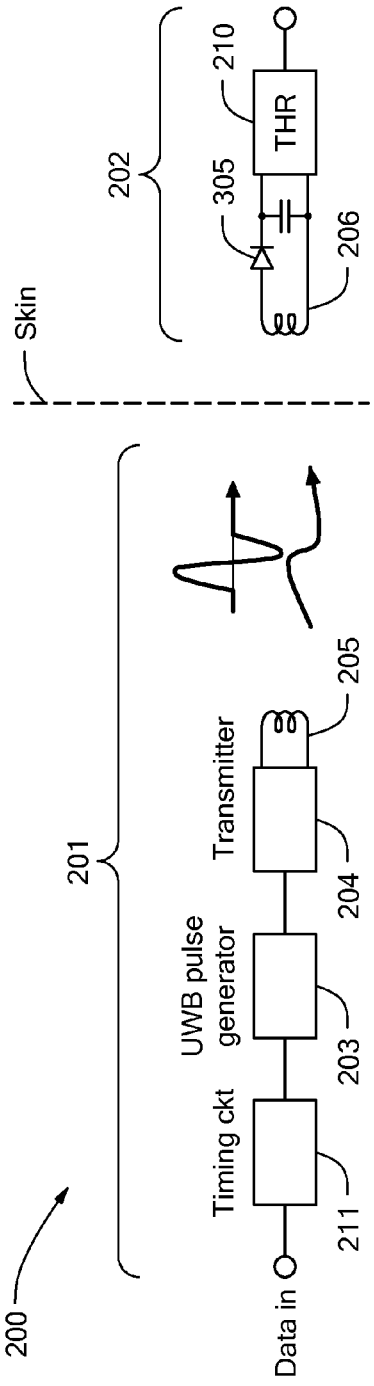

LOW POWER SIGNAL TRANSMISSION

PRIORITY

This application is a continuation of U.S. patent application Ser. No. 12/652,335, filed Jan. 5, 2010, entitled "Low Power Signal Transmission," which is now U.S. Pat. No. 8,363,867, which in turn is a divisional of U.S. patent application Ser. No. 10/452,828, filed Jun. 2, 2003, entitled "Low Power Signal Transmission," which is now U.S. Pat. No. 7,657,045, which in turn claims priority from U.S. Provisional Application No. 60/384,948, filed May 31, 2002, entitled "Low Power Signal Transmission Over Short Distances." Each of the above-described applications is incorporated herein by reference, in its entirety.

TECHNICAL FIELD

The present invention relates to low power signal transmission over short distances, which may be used, for example, in implanted devices such as a cochlear implant.

BACKGROUND ART

With implanted devices it may be necessary to transmit information to the implant over a comparatively short distance during an extended period of time.

An example for such an application is the transmission of speech information to a fully implanted cochlear implant 101 from an external device 102, such as a microphone 103 and/or a processor 104 placed behind the ear or in the ear canal, as shown in FIG. 1. Since the transmitter 105, as well as the receiver 106, are powered from small batteries 107 and 108 contained in the external device 102 and in the implant 101, respectively, both the power consumption of the transmitter 105 as well as of the receiver 106 become limiting factors.

Another application could be the transfer of information between bilateral ear level microphones and/or processors used with hearing aid or cochlear implant applications. In these cases a comparison or a common processing of left and right speech signals may be necessary either for beamforming or for coordinated processing schemes in order not to distort direction information.

Referring to FIG. 1, a cochlear implant transmission system typically includes an Radio Frequency (RF) transmitter 105 that drives an external coil 109 with a modulated RF signal. This signal is picked up by a receiver's 106 implanted coil 110, which may be located at only a few mm or cm from the transmitter coil 109, and further processed by the receiver 106. With conventional narrow band RF transmission schemes using well known modulation methods for transmission of speech signals of considerable dynamic range (e.g. 70-90 dB) either as an analog signal or a coded signal (e.g. PCM or encoded in a $\Sigma\Delta$-modulator-data stream, typical band width 1 . . . 2 MHz), the power consumed either by the transmitter 105 or by the receiver 106 (e.g. when using a very low power transmitter delivering a very faint signal making a large RF amplification necessary), or both, may turn out to be prohibitive. Note that the overwhelming percentage of the total power consumption results from the RF components at the transmitting and/or receiving end. The power consumption of processing in the baseband is negligible due to the low speed power product of modern CMOS technology and the comparative low frequencies of the baseband.

Very low power receivers may utilize, for example, diode rectifiers. However, the threshold voltage of the diode rectifier may be too large, even when using backward diodes for demodulation. Another very low power receiver is the super-regenerative receiver, which does not have sufficient bandwidth for transmission of coded speech signals. Examples of still other receivers include superheterodyne or the homodyne receivers, or a straight amplifier chain preceding a demodulator. However, in each of these cases the power consumption of the RF amplification is non-negligible. Depending on the transmitter power selected, the relative proportion of transmitter power to receiver power may be adapted to the respective battery capacity available. For example, a strong transmitted signal may require small or even no amplification at the receiver. However, total power consumption may be too large in any event.

SUMMARY OF THE INVENTION

In a first embodiment of the invention there is provided a method and system for a low-power implant system. An implant, for implantation into a person, is capable of communicating via transmission of ultra wideband pulses. A device is capable of communicating with the implant via ultra wideband pulse transmission.

In related embodiments, the implant and the device are capable of one of unidirectional and bidirectional communication via ultra wideband pulse transmission. The implant may be a cochlear implant or a middle ear implant. The device may be adapted to be worn external to the person, and include: a signal processor for processing an acoustic signal; and a transmitter capable of transmitting the pulses representative of the acoustic signal through the skin of the person to the implant. The implant may include at least one electrode and be capable of providing electrical stimulation via the at least one electrode as a function of the acoustic signal received from the transmitter. The device may be a second implant for implantation into the person. The implant and the device may communicate via ultra wideband pulses having: a duty cycle of approximately 1/1000 or less; a time duration of between 0.5 ns and 10 ns; and/or a pulse repetition time between 5 and 100 μs.

In still other related embodiments of the invention, the device includes one of a transmitter capable of transmitting ultra wideband pulses and a receiver capable of receiving ultra wideband pulses, and the implant includes the other of the transmitter and the receiver. The receiver may include a time-gated amplifier, the amplifier for amplifying the pulses received from the transmitter. The time-gated amplifier may be turned on when a probability of receiving a pulse from the transmitter is greater than zero. The time-gated amplifier may be biased so as not to be completely off when a probability of receiving a pulse from the transmitter is zero. The time-gated amplifier may turn on periodically for a time duration D, the turning on of the amplifier synchronized with possible receipt of a pulse from the transmitter. The time-gated amplifier may include a controller for synchronizing turning on of the amplifier during possible receipt of a pulse from the transmitter. The controller may synchronize the gated amplifier with pulses received from the transmitter based on receipt of a pulse with a predefined amplitude and/or duration. The amplifier may be a differential amplifier or a pseudo-differential amplifier. The receiver may be a passive receiver. The transmitter and receiver may each include a coil or loop for transmission between the transmitter and the receiver via inductive coupling. The receiver may include a nonlinear electronic component for converting RF components, transmitted via ultra wideband pulses, back to baseband. The transmitter may directly transmit, via ultra wideband pulses, a baseband signal. The transmitter may transmit ultra wideband monocycle pulses, thus eliminating low-frequency spectral components. Due to resonances of the transmitter and/or receiver antenna coils certain high frequency components of the signal may become emphasized, thus producing damped RF bursts from each wideband pulse.

In another embodiment of the invention, a method and system for a low-power hearing system includes a first external signal processor for providing information to one of a hearing aid and an implant. A second external signal processor is capable of communicating with the first external signal processor via ultra wideband pulses.

In related embodiments of the invention, the ultra wideband pulses may have: a duty cycle of 1/1000 or less; have a time duration of between 0.5 ns and 10 ns; and/or have a pulse repetition time between 5 and 100 µs. The first external processor and/or the second external processor may have a receiver for receiving the ultra-wideband pulses, the receiver including a time-gated amplifier. The time-gated amplifier may include a controller for synchronizing turning on of the receiver with possible receipt of a ultra wideband pulse. The controller may synchronize the gated amplifier with pulses received based on receipt of a pulse with a predefined amplitude or duration.

In still another related embodiment, the first external signal processor may include a first microphone, and the second external signal processor include a second microphone. The first signal processor processes an acoustic signal present in a first ear of a user and the second signal processor processes an acoustic signal present in the second ear of the user.

BRIEF DESCRIPTION OF THE DRAWINGS

The foregoing features of the invention will be more readily understood by reference to the following detailed description, taken with reference to the accompanying drawings, in which:

FIG. 2 is a schematic diagram of a low-power implant system that includes transmission of UWB pulses, in accordance with one embodiment of the invention;

FIG. 3 is a schematic diagram of a low-power implant system that includes transmission of UWB monocycle pulses, in accordance with one embodiment of the invention;

DETAILED DESCRIPTION OF SPECIFIC EMBODIMENTS

Figure 1:
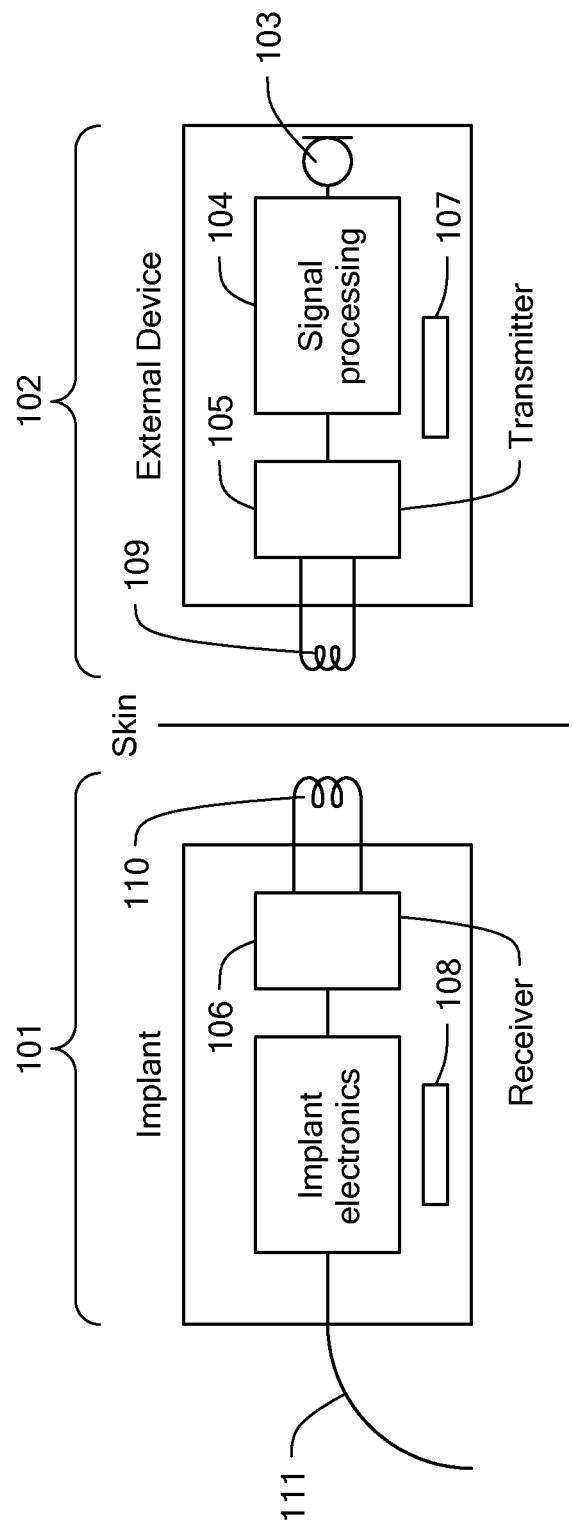
FIG. 1 is a schematic diagram of a prior art system for transmitting acoustic information to a fully implantable cochlear implant from a signal processor placed behind the ear.

In illustrative embodiments of the invention, a system and method for low power signal transmission between, for example, parts of a hearing system, is presented. The low power signal transmission is achieved by transmitting very short ultra wideband (UWB) pulses. In various embodiments, the transmitted UWB signals are representative of signals having a bandwidth not exceeding 1 or 2 MHz. The UWB pulses can thus be transmitted at a very small duty cycle, resulting in very low transmitter power consumption. Additional power savings are realized at the receiver by using passive receivers or gated receivers which are synchronized to the incoming UWB pulses. Details of illustrative embodiments are discussed below.

Ultra Wideband (UWB) technology is a relatively new communication technology that is fundamentally different from communication using modulated methodologies. See for example, U.S. Pat. No. 6,031,862, entitled "Ultra-wideband Communication System and Method," which is herein incorporated by reference. Rather than employing a carrier signal, UWB emissions are composed of a series of short, intermittent pulses having a pulse duration on the order of picoseconds or nanoseconds. By varying the pulses' amplitude, polarity, timing and/or other characteristic, information is coded into the data stream. Various other terms have been used for the UWB transmission mode—carrierless, baseband, nonsinusoidal and impulse-based among them.

However, UWB has traditionally been used at high data transmission rates. For example, UWB radios typically perform at well over 100 Mbps. Because UWB pulses are so short, high data rates can be achieved by spacing the pulses close together.

FIG. 2 is a schematic diagram of a low-power implant system 200 that includes transmission of UWB pulses, in accordance with one embodiment of the invention. The low-power implant system includes an implant 202 for implantation into a person. The implant 202 may be, without limitation, a cochlear implant, a brainstem implant, or a middle ear implant. Additionally, the low-power implant system 200 includes a device 201 capable of communicating with the implantable portion 202 via transmission of UWB pulses. The device may be may adapted to be worn external to the person, such as a signal processor for processing acoustic signals. Or the external device may be a more distant device relative to the person, such as an FM sound amplification device or a TV set. In still other embodiments, the device 201 may be another implant. Communication may be bi-directional, or uni-directional in either direction.

The device 201 includes a timing circuit 211 that triggers a pulse generator 203. The pulse generator 203 generates a UWB pulse that is transmitted via a transmitter 204 to the implant 202. The implant 202 includes a receiver 210 for receiving the transmitted UWB pulse. Both the transmitter 204 and receiver 210 may include a coil or loop 205 and 206, respectively, such that pulse transmission between the transmitter 204 and the receiver 210 is via inductive coupling. In other embodiments, transmission may be via electric dipoles, however their use may prove to be problematic with regard to body tissue in close proximity to the implant 202.

As described above, the implant may be a cochlear implant (inner ear prostheses), in accordance with one embodiment of the invention. Cochlear implants are a means to help profoundly deaf or severely hearing impaired persons. Unlike conventional hearing aids, which just apply an amplified and modified sound signal, a cochlear implant is based on direct electrical stimulation of the acoustic nerve. The intention of a cochlear implant is to stimulate nervous structures in the inner ear electrically in such a way that hearing impressions most similar to normal hearing are obtained.

The cochlear implant system essentially consists of two parts, an external device which acts as the speech processor and the implant which acts as a stimulator. The speech processor receives and performs signal processing on an acoustic signal. The processed acoustic signal is then transmitted to and received by the implant. The implant generates the stimulation patterns and conducts them to the nervous tissue by means of an electrode array 111 (see FIG. 1) which usually is positioned in the scala tympani in the inner ear.

The processed acoustic signal transmitted is typically digitized/coded using, for example, $\Sigma$-$\Delta$ modulation (other embodiments may use more complex signal coding, such as Pulse Code Modulation, and also differentiate between pulses carrying signal information and pulses transmitted for synchronization only), and may have a bandwidth of approximately 1-2 MHz (in certain embodiments, only signal-amplitude-derived control signals are transferred, allowing for a bandwidth not exceeding a few kHz). This baseband signal may be used to directly drive the transmitter 204 so as to transmit single-phase baseband UWB pulses, as shown in FIG. 2.

Due to the low data rate, the resulting UWB pulses are transmitted at a very low duty cycle. Consequently, the transmitter 204 components consume relatively little power. The pulses received at the receiver 210 are detected, possibly amplified, and can be processed by conventional digital CMOS circuitry. A threshold to eliminate low level interference signal can be obtained, for example, by proper biasing of CMOS gates or by the use of a Schmitt-trigger circuit.

In various embodiments, the simple baseband detection scheme described above is replaced by more complex schemes using for example, nonlinear element(s) with pre and/or post rectification amplifiers. For example, FIG. 3 is a schematic diagram of a low-power implant system 200 that includes transmission of UWB monocycle pulses. These pulses are advantageous as they do not contain low-frequency spectral components. Low-frequency spectral components are inefficiently transmitted via antennas and cause substantial ringing. A non-linear element 305 rectifies and generates the base-band pulse from the RF signal, such as, without limitation, a diode, a backward diode, or a Schottky-diode.

Figure 4:
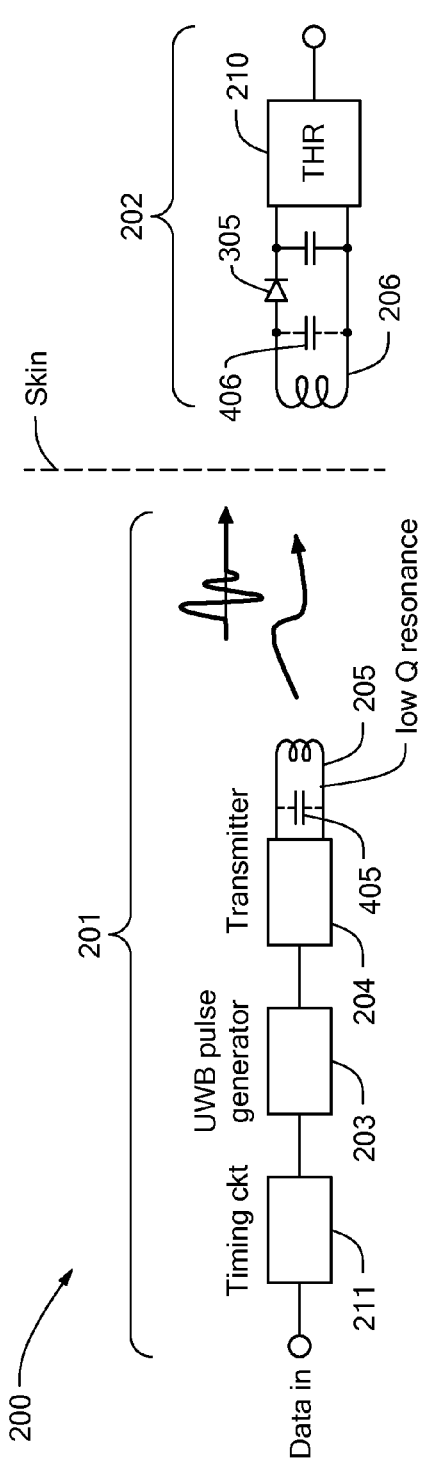
FIG. 4 is a schematic diagram of a low-power implant system that includes low Q resonance, in accordance with one embodiment of the invention.

The coils/loops of the transmitter 204 and receiver 210 together with additional capacitance 405 or with stray capacitance may be utilized to provide a comparatively low Q resonance, as shown in FIG. 4, in accordance with one embodiment of the invention. The low Q resonance can be used to enhance receiver input signals and thus improve transmission. Care must be taken to not unduly prolong transmission pulses. This could lead to a reduction in data rate and power savings when certain types of receivers are implemented.

In various embodiments of the invention, a passive receiver can be utilized. The output pulses are further processed by digital CMOS-logic, including a trigger circuit to establish a reasonable threshold. Although passive receivers are easy to implement, a passive receiver is relatively insensitive, and can be utilized only for distances within the range of, for example, several centimeters. For larger distances, the passive receiver requires that sufficient pulse amplitudes are generated by the UWB transmitter. Therefore, when only very low transmitter power is available and/or for greater distances, the receiver must be more sensitive. This can be achieved by a widebandamplifier preceeding the detector. However, such an amplifier uses a disproportionately large supply of current. The resulting power consumption may well dominate the power consumption of the whole system.

Figure 5:
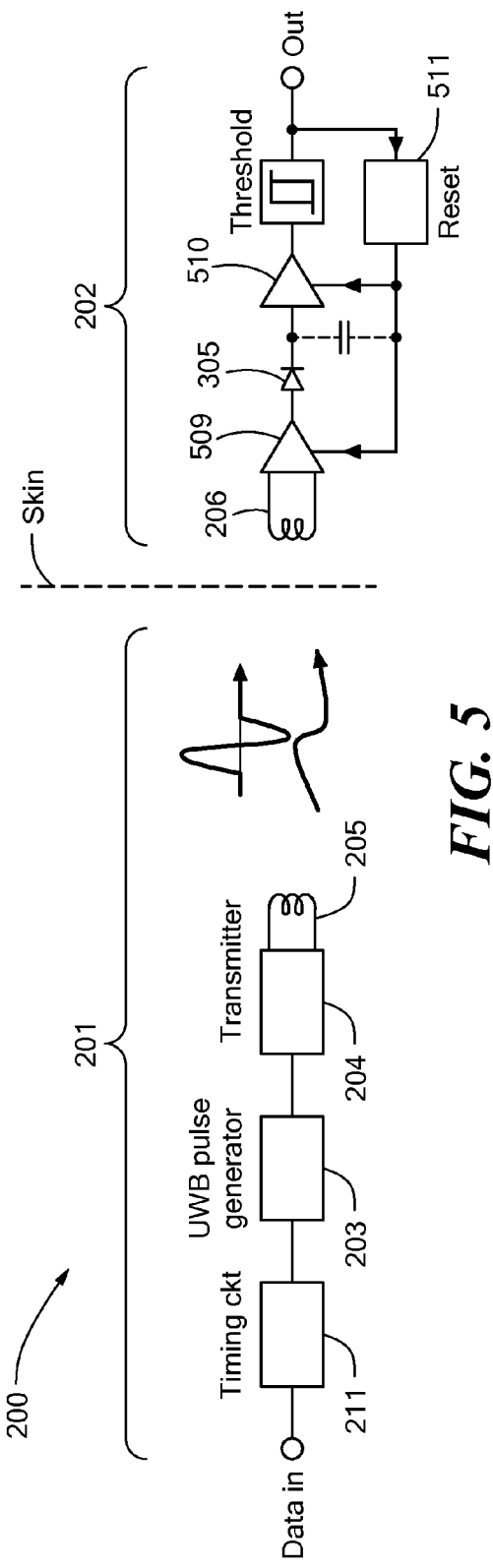
FIG. 5 is a schematic diagram of a low-power implant system that includes an active receiver, in accordance with one embodiment of the invention.

FIG. 5 is a schematic diagram of a receiver that utilizes an amplifier(s) to advantageously increase receiver sensitivity, in accordance with one embodiment of the invention. An amplifier 509 may precede rectifier 305 (if needed). Alternatively, or in combination with amplifier 509, an amplifier 510 may follow rectifier 305.

To conserve power, the amplifier(s) 509 and/or 510 are time-gated so as to switch the amplifier(s) on only during short intervals when the likelihood for reception of a signal pulse is not zero. Unlike traditional gating of receivers, which is done to improve signal to noise ration and to block echoes arriving later than the direct signal, the emphasis here is to conserve power at the receiver. Gating of the amplifiers 509 and/or 510 may be accomplished by a controller 511, which provides an amplifier turn-on pulse that is synchronized with the transmitted signal pulses.

Figure 6:
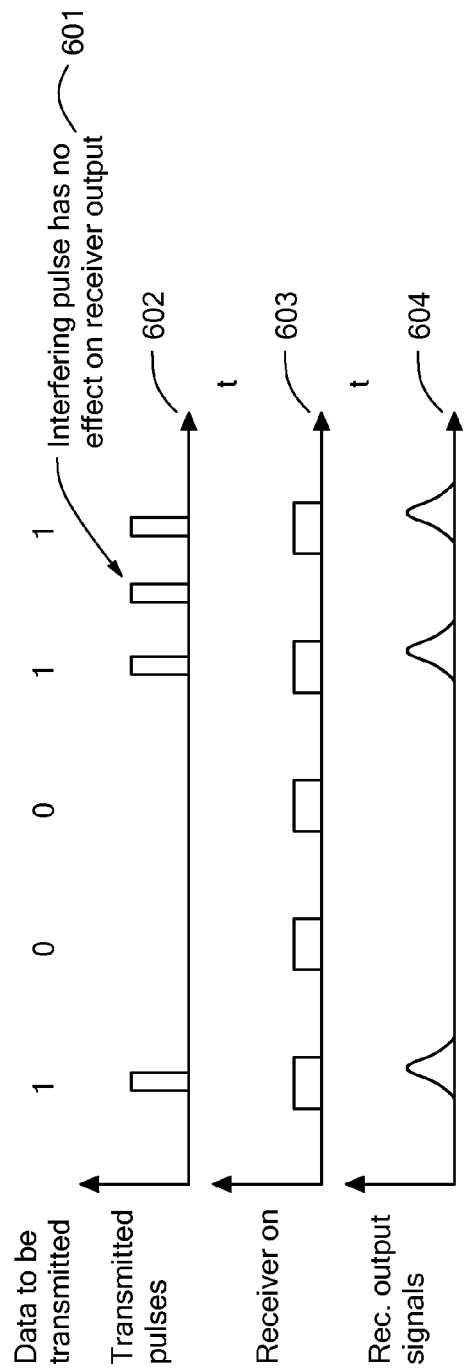
FIG. 6 shows a timing diagram detailing the timing of a gated receiver of a low-power implant system, in accordance with one embodiment of the invention.

FIG. 6 is an exemplary timing diagram that illustrates the timing relationships between the data to be transmitted 601, the transmitted signals 602, the amplifier turn-on pulse 603 generated by the controller 511, and the receiver output signals 604. The transmitted signals are transmitted at a rate 1/T, with a pulse transmitted depending on whether the data to be transmitted is a logic 1 or 0. The amplifier turn-on pulses are synchronized with the possible receipt of pulses transmitted by the transmitter. A transmitted pulse received during activation of a turn-on pulse will be detected and seen at the receiver output 604, while pulses received while the turn-on pulse is inactive have no effect on receiver output 604.

Figure 7:
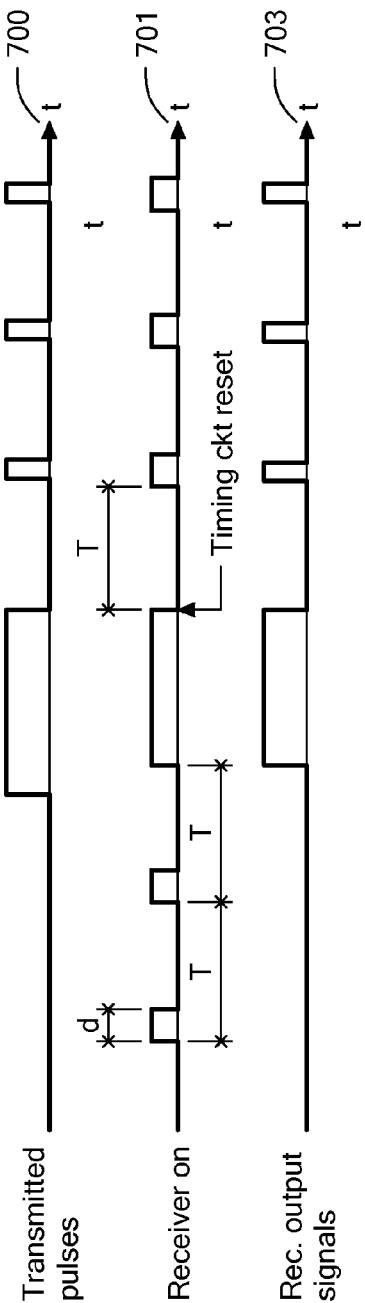
FIG. 7 shows a timing diagram detailing synchronization timing of a gated receiver of a low-power implant system, in accordance with one embodiment of the invention.

A timing diagram detailing synchronization of the amplifier turn-on pulse 701 with possible receipt of transmitter pulses 700 is shown in FIG. 7, in accordance with one embodiment of the invention. Initially, the amplifier turn-on pulses 701 are activated at a periodic rate of 1/T, with each turn on-pulse 701 having a time duration d. At the beginning of a transmission, the transmitter transmits a pulse having duration slightly longer than T. The receiver receive at least a part of this long pulse while the turn-on pulse 701 is activated, and will recognize that a pulse has been received having a duration longer than d. This triggers the controller to keep the amplifier turn-on pulse 701 active until the end of the transmitted long pulse. This is the event which causes the controller to reset and synchronize the amplifier turn-pulse 701 with the possible receipt of transmitter pulses 700. After the time T, the controller will activate the turn-on pulse 701 so to receive the first possible signal pulse of the transmission. Once the controller has established synchronization between the turn-on pulse 701 and transmitted pulses 700, the controller will maintain synchronization for the duration of the transmission using, without limitation, a phase locked loop or a resettable timing generator, which may be synchronized by each received pulse (if no pulse is received, the controller mayl run free until synchronized by the next correctly received pulse). Receiver output 703 is as described above with regard to FIG. 6.

Other synchronization methodologies may be utilized. For example, the transmitter may transmit an extra strong pulse which is received even when the amplifier(s) are in low power mode (i.e. when the turn-on pulse is inactive), in accordance with one embodiment of the invention. The extra strong pulse forces the controller to synchronize the turn-on pulse with possible receipt of transmitted pulses. In this embodiment, the amplifier(s) is not turned completely off when the turn on pulse is inactive. Instead, a small quiescent current is maintained such that the extra strong pulse can be recognized by the receiver.

In preferred embodiments, the pre and post rectification amplifiers are differential amplifiers or pseudo-differential amplifiers. This prevents the turn-on pulse (which is applied common mode) from reaching a predetermined pulse detection threshold. Although there will be some unavoidable feed through due to transistor tolerances, only transmitted signal pulses, which occur when the turn-on pulse is active, will be detected.

Figure 8:
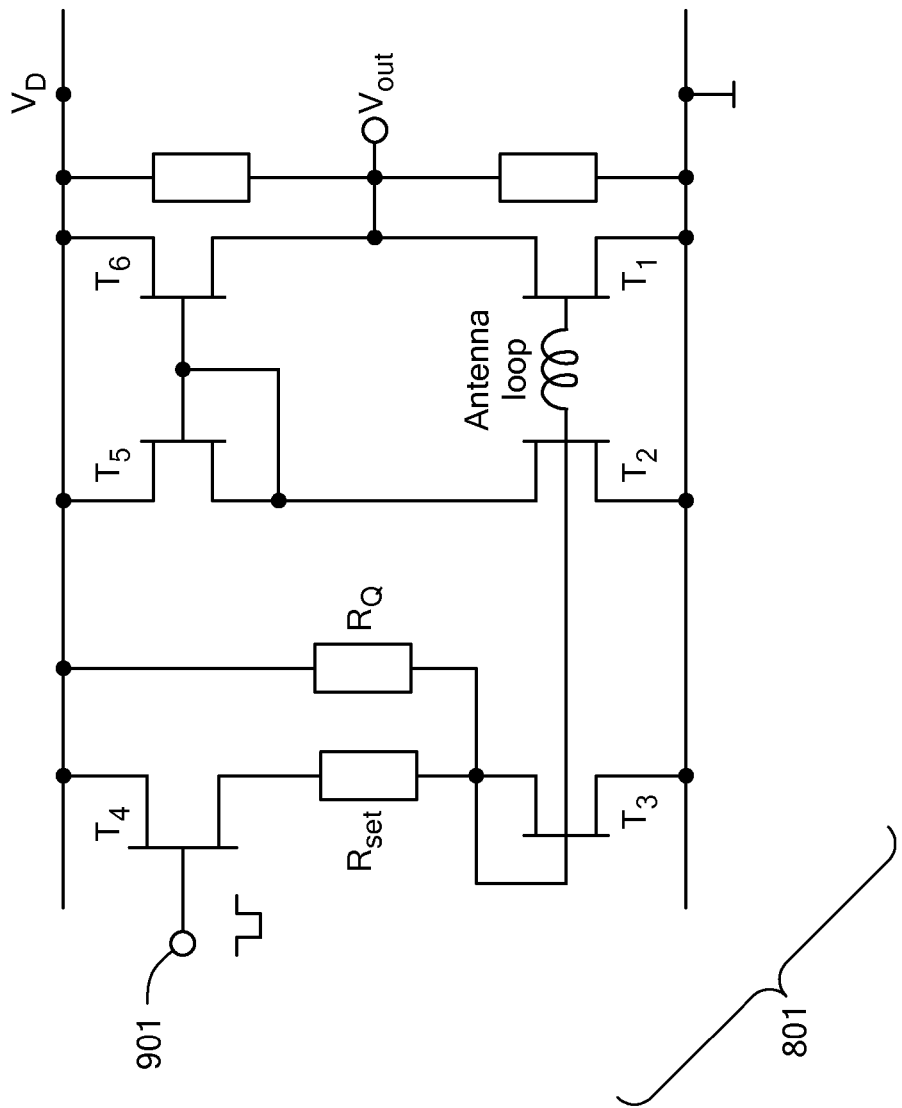
FIG. 8 is a schematic diagram of a gated amplifier for a low-power implant system, in accordance with one embodiment of the invention.
Figure 9:
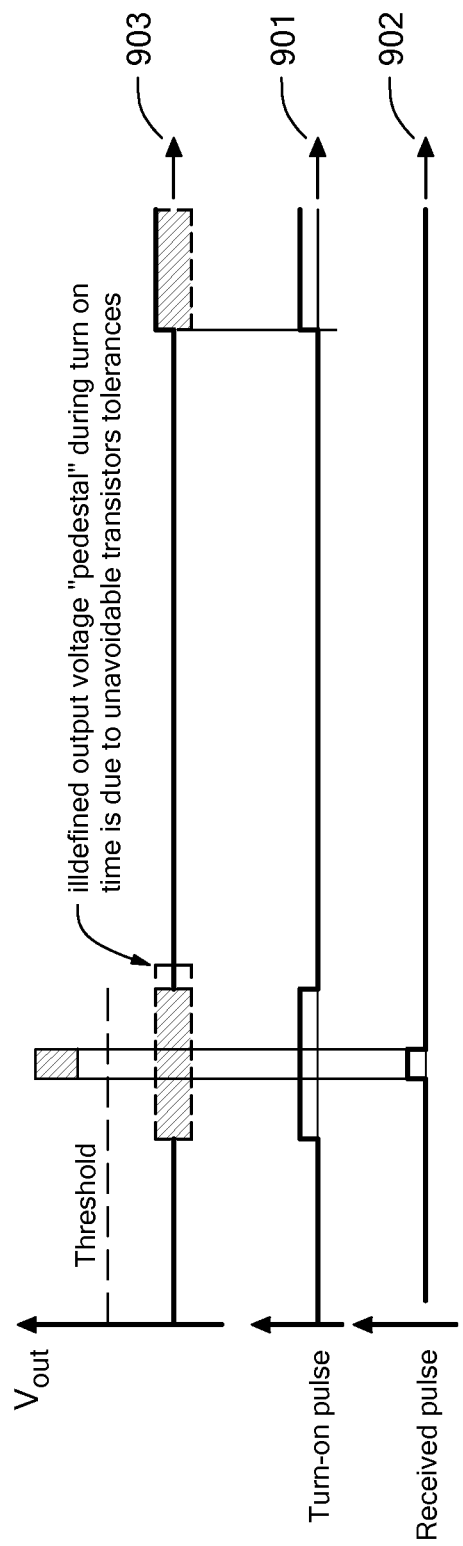
FIG. 9 is a timing diagram detailing the timing associated with the gated amplifier depicted in FIG. 8, in accordance with one embodiment of the invention.

In accordance with one embodiment of the invention, FIGS. 8 and 9 show a schematic diagram and an associated timing diagram for a gated amplifier 801, respectively. CMOS-technology is used. $T_1 \ldots T_3$ are n-channel MOS-transistors, and $T_4 \ldots T_6$ are p-channel transistors. $T_1$, $T_2$, $T_5$ and $T_6$ form a pseudo-differential amplifier. $T_3$ and $T_4$ are part of the biasing circuitry and are used to turn on the amplifier to make the receiver receptive for the transmitted UWB pulses.

"Diode-connected" transistor $T_3$ is slightly forward biased by the small current defined by $R_Q$ and the supply voltage $V_D$. Since the gates of $T_1$, $T_2$ and $T_3$ are connected; $T_2$ and $T_3$ see the same gate voltage and therefore carry the identical small quiescent dc-currents. The well known current mirror formed by $T_5$ and $T_6$ generates a drain current at $T_6$ which ideally is equal to the drain current of $T_1$. The quiescent output voltage is defined by the relative output resistances of $T_1$ and $T_6$. To make the amplifier more independent of transistor parameter tolerances, external resistors $R_1$ and $R_2$ may be added.

To obtain significant amplification, larger drain currents are needed. Therefore, to turn the amplifier 801 on, a turn-on pulse 901 is applied to $T_4$. The current through $R_{set}$ enhances the forward biasing of $T_3$ and consequently enlarges all currents to an appropriate level. Activation of the turn-on pulse without receipt of a transmitted pulse must result in an output voltage 903 smaller than the threshold of the decision circuit following the amplifier. However, when a pulse 902 is received during activation of the turn-on pulse 901, the voltage being induced in the antenna loop/coil will cause a change in the gate voltage of T1. This, in turn, causes a change in T1's drain current that results in an output voltage 903 that is sufficient to trigger the decision circuit.

Figure 10:
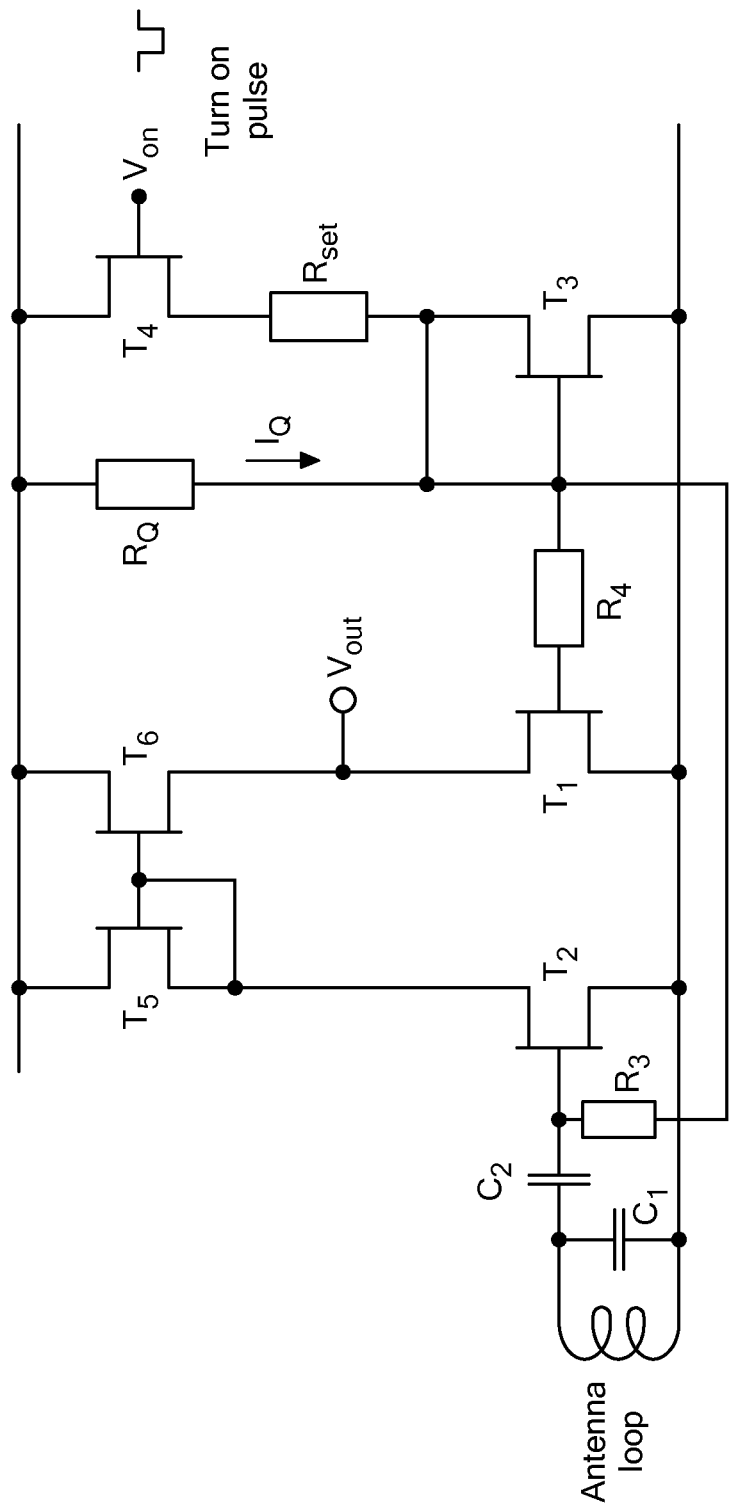
FIG. 10 is a schematic diagram of a gated amplifier for a low-power implant system that receives monocycle pulses, in accordance with one embodiment of the invention.

In accordance with another embodiment of the invention, FIG. 10 is a schematic diagram of a pseudo-differential amplifier for a receiver that receives monocycle pulses or short RF-bursts, as shown in FIG. 5. The receiver antenna loop/coil forms a low Q resonance with capacitor $C_1$, which at least partly consists of stray capacitance. Capacitor $C_2$ prevents the gate voltage of $T_1$ from being shorted by the antenna loop. In principle the function of this circuit is equivalent to the circuit described in FIG. 8. The main difference is that, in order to make efficient use of the RF components of the received spectrum, the biasing must ensure that $T_1$ is driven in a sufficiently nonlinear part of its transfer characteristic so that some rectification of RF components is achieved. Resistors $R_3$ and $R_4$ connect the gates of $T_1$ and $T_2$ to $T_3$ without disturbing the RF signal.

Figure 11:
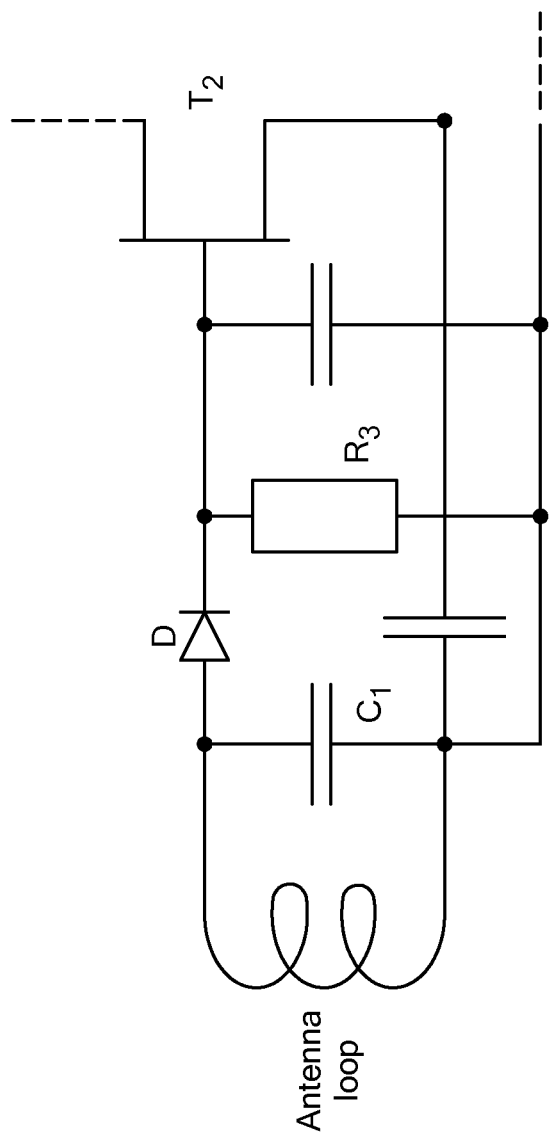
FIG. 11 is a schematic diagram of a rectifier for a gated amplifier, in accordance with one embodiment of the invention.

Rectification of RF components may also be accomplished by the circuit shown in FIG. 11, in accordance with one embodiment of the invention. Here, an extra diode D is used for the rectification of RF components of the received pulse.

Figure 12:
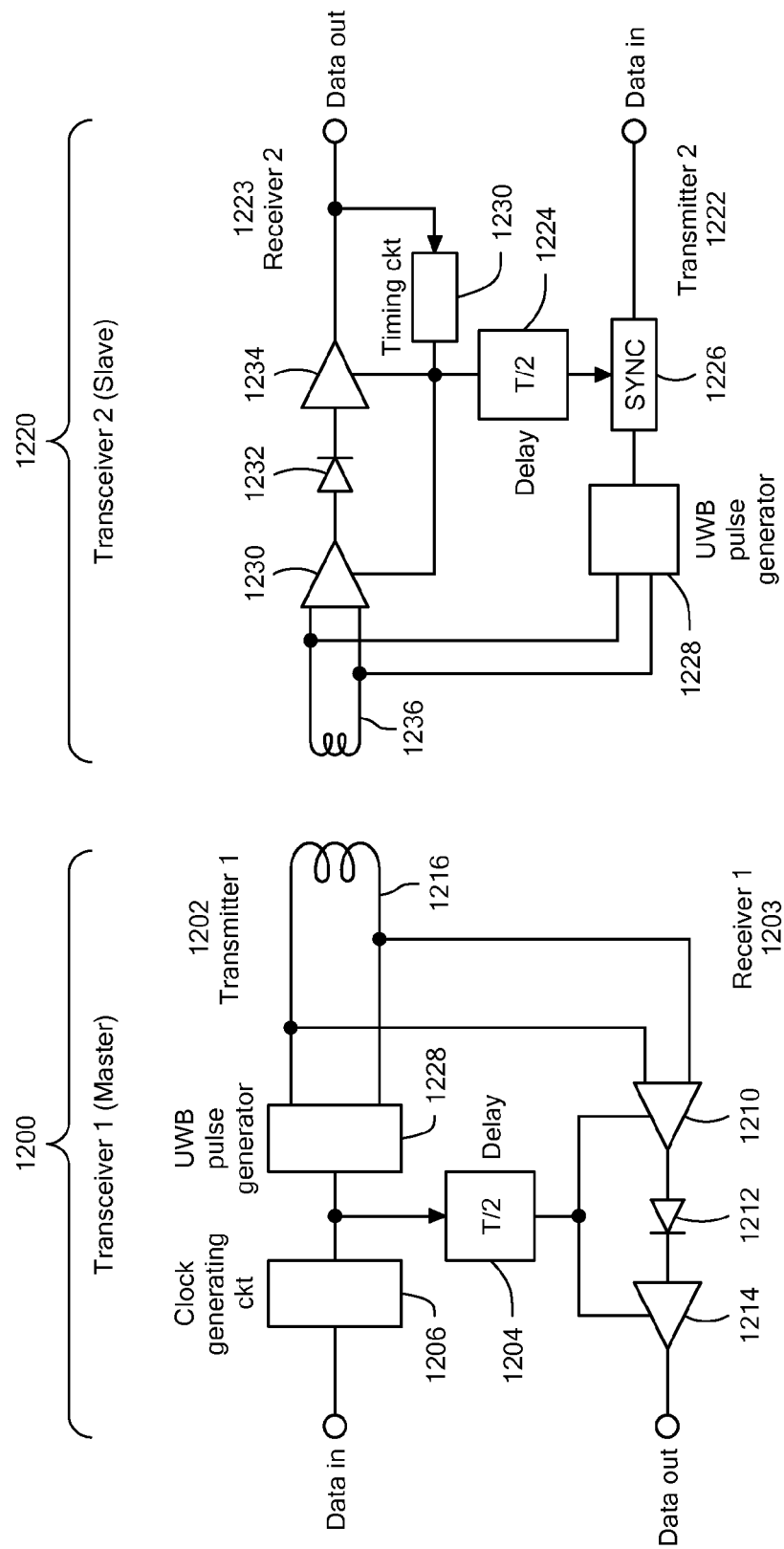
FIG. 12 is a schematic diagram of a low-power implant system that includes duplex transmission, in accordance with one embodiment of the invention.
Figure 13:
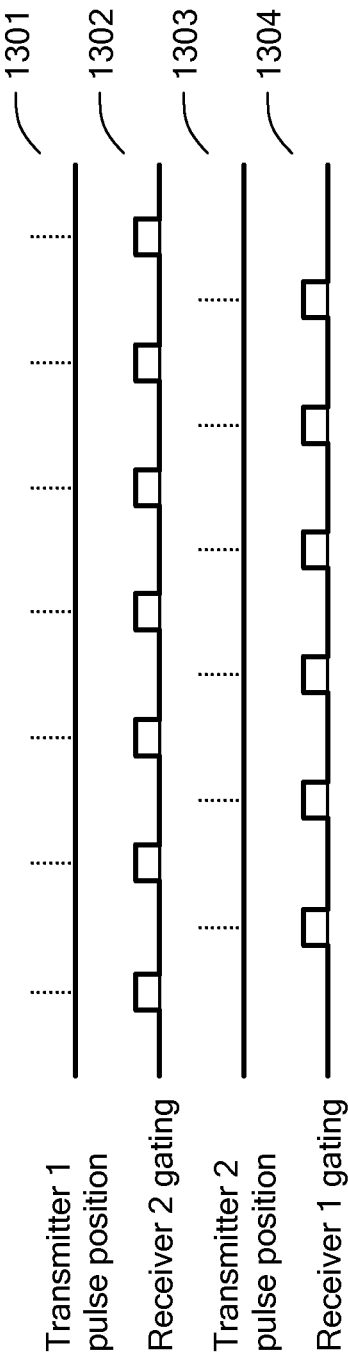
FIG. 13 is a timing diagram detailing the timing of the low-power implant system of FIG. 12, in accordance with one embodiment of the invention.

FIG. 12 is a schematic diagram of an exemplary duplex low-power implant system between a first transceiver 1200 and a second transceiver 1220, in accordance with one embodiment of the invention. Each transceiver 1200 and 1220 includes a transmitter 1202 and 1222 and a receiver 1203 and 1223 that share the same loop/coil 1216 and 1236, respectively. Additionally, each transmitter 1202 and 1222 includes a clock generating circuit 1206 and 1226 and a UWB pulse generator 1208 and 1228, respectively; and each receiver 1203 and 1223 includes a pre-rectification amplifier 1210 and 1230, a rectifying diode 1212 and 1232, and a post-rectification amplifier 1214 and 1234, respectively. FIG. 13 is a timing diagram detailing the timing for the duplex transmission scheme shown in the embodiment of FIG. 12.

Referring to FIGS. 12 and 13, the first transceiver ("master") 1200 sets the timing for the transmission of signals in both directions. The second transceiver's 1220 timing ("slave") can be locked to the received transmission pulses by controller 1230 logic generating turn-on pulses 1302 as described above, for example, with regard to FIG. 7.

In order to use the same inductive link for both directions, the pulses 1301 transmitted by the first transmitter 1202 and the pulses 1303 transmitted by second transmitter 1222 are interleaved. To achieve this offset Δ (e.g. Δ=T/2) a delay circuit 1224 is introduced in the second transceiver 1220 to delay the pulses 1303 generated by second transmitter 1222 by T/2. Similar delay circuitry 1204 is utilized in the first transceiver 1200 to appropriately delay the gating (turn-on pulse) 1304 of the receiver 1203 associated with the first transceiver 1200. Since all signals are derived from the pulses 1301 generated by the first transmitter 1202, no controller logic for providing synchronization is needed in the first transceiver 1200.

The low bandwidth of the signals transmitted to and/or from the implant allows the UWB pulses to be transmitted at a very low duty cycle, conserving power at the transmitter. Time-gating the amplifiers in the implant and/or device receiver also conserves power at the receiver. Approximate parameter ranges of a typical hearing system that includes communication via UWB pulses transmissions are, without limitation:

| Pulse duration (of transmitter UWB-pulse) | τ | 1...10 nsec |
|---|---|---|
| Pulse repetition time | T | 1...10 μsec |
| "turn-on pulse" duration | d | 5...100 μsec |
| duty factor of transmission pulse | τ/T | approx. 1:1000 |
| duty factor of receiver gating | d/T | approx. 1:100 |
| delay between forward and backward transmission pulses in a duplex arrangement | Δ | e.g. T/2 (see FIG. 13) |

In accordance with another embodiment of the invention, a low-power hearing system may include UWB communication between parts external to the person. For example, data can be transferred, in a manner similar to the above-described embodiments, between a plurality of external devices, such as bilateral microphones and/or external signal processors that are positioned, for example, behind each ear or other various locations. The external device(s) can thus perform acoustic beamforming or other coordinated schemes. The external devices may be used, for example, in conjunction with a hearing aid and/or an implant.

Although various exemplary embodiments of the invention have been disclosed, it should be apparent to those skilled in the art that various changes and modifications can be made which will achieve some of the advantages of the invention without departing from the true scope of the invention. These and other obvious modifications are intended to be covered by the appended claims.

What is claimed is:

1. A method of low-power communication for a hearing system that includes a hearing implant associated with a first ear of a user, the hearing system further including an external signal processor, the method comprising:
   transmitting pulses by one of the hearing implant and the external signal processor;
   receiving the pulses at an input to a time-gated amplifier of the other one of the hearing implant and the external signal processor, the amplifier for amplifying the pulses received at the input; and
   synchronizing turning on of the time-gated amplifier with the possible receipt of transmitted pulses based, at least in part, on a transmitted pulse received at the input.

2. The method according to claim 1, wherein transmitting includes transmitting ultra wideband pulses at a duty cycle of approximately 1/1000 or less.

3. The method according to claim 1, wherein transmitting includes transmitting ultra wideband pulses having a time duration of between 0.5 ns and 10 ns.

4. The method according to claim 1, wherein transmitting includes transmitting pulses at a pulse repetition time between 5 and 100 μs.

5. The method according to claim 1, wherein the synchronizing includes turning on the amplifier when a probability of receiving a pulse is greater than zero.

6. The method according to claim 5, wherein the synchronizing includes biasing the amplifier so as not to be completely off when a probability of receiving a pulse is zero.

7. The method according to claim 1, wherein synchronizing the turning on of the amplifier with possible receipt of transmitted pulses is based on receipt of a pulse with a predefined amplitude.

8. The method according to claim 1, wherein synchronizing the turning on of the amplifier with possible receipt of transmitted pulses is based on receipt of a pulse with a predefined duration.

9. The method according to claim 1, wherein the external signal processor is operatively coupled to a microphone, the method further including:
   processing, at the external signal processor, an input signal received from the microphone, the input signal representative of an acoustic signal present in a second ear of the user; and
   transmitting from the external signal processor to the hearing implant pulses associated with the processed input signal to the hearing implant.

10. The method according to claim 9, further comprising a second external signal processor associated with the first ear of the user, the second external signal processor operatively coupled to a second microphone, the method further comprising:
    processing, at the second external signal processor, a second input signal representative of an acoustic signal present in the first ear of the user; and
    transmitting from the second external signal processor to the hearing implant, pulses associated with an acoustic signal present in the first ear of the user, to the hearing implant.

11. The method according to claim 1, wherein the hearing implant is one of a cochlear implant and a middle ear implant.

12. A method of low-power communication, the method comprising:
    transmitting pulses by one of a first signal processor and a second signal processor;
    receiving the pulses at an input to a time-gated amplifier of the other one of the first signal processor and the second signal processor, the amplifier for amplifying the pulses received at the input; and
    synchronizing turning on of the time-gated amplifier with the possible receipt of transmitted pulses based, at least in part, on a transmitted pulse received at the input.

13. The method according to claim 12, wherein the first signal processor is implanted in a user, and the second processor is external to the user.

14. The method according to claim 13, wherein the first signal processor is associated with one of a cochlear implant and a middle ear implant.

15. The method according to claim 12, wherein the first signal processor is external to the user and provides information to one of a hearing aid and a hearing implant, and the second signal processor is external to the user.

16. The method according to claim 12, wherein transmitting includes transmitting ultra wideband pulses.

17. The method according to claim 12, wherein the synchronizing includes turning on the amplifier when a probability of receiving a pulse is greater than zero.

18. The method according to claim 12, wherein the synchronizing includes biasing the amplifier so as not to be completely off when a probability of receiving a pulse is zero.

19. The method according to claim 12, wherein synchronizing the turning on of the amplifier with possible receipt of transmitted pulses is based on receipt of a pulse with a predefined amplitude.

20. The method according to claim 12, wherein synchronizing the turning on of the amplifier with possible receipt of transmitted pulses is based on receipt of a pulse with a predefined duration.

* * * * *